(12) United States Patent
Jones et al.

(10) Patent No.: US 6,514,710 B1
(45) Date of Patent: *Feb. 4, 2003

(54) METHOD OF USING CYCLIC PEPTIDES TO INHIBIT BINDING TO UROKINASE-TYPE PLASMINOGEN ACTIVATOR RECEPTOR

(75) Inventors: Terence R. Jones, San Diego, CA (US); David N. Haney, Mercer Island, WA (US); Janos Varga, Napa, CA (US)

(73) Assignee: Angstrom Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/285,783

(22) Filed: Apr. 5, 1999

Related U.S. Application Data (62) Division of application No. 08/747,915, filed on Nov. 12, 1996, now Pat. No. 5,942,492.

(51) Int. Cl.[7] .................. A61K 38/12; A61K 38/10; G01N 33/53
(52) U.S. Cl. ............... 435/7.2; 514/2; 514/11
(58) Field of Search ............... 435/7.2; 514/2, 514/11

(56) References Cited

U.S. PATENT DOCUMENTS 6,277,818 B1 * 8/2001 Mazar et al.

FOREIGN PATENT DOCUMENTS

| WO | WO 90/12091 | 10/1990 |
| WO | WO 94/22464 | 3/1994 |
| WO | WO 94/28014 | 5/1994 |
| WO | WO 94/28014 | 12/1994 |
| WO | WO 94/28145 | 12/1994 |

OTHER PUBLICATIONS

Appella, E. et al., *J. Biol. Chem.*, 262:4437–40 (1987).
Behrendt, N. et al., *Biol. Chem. Hoppe–Seyler*, 376:269–79 (1995).
Behrendt, N. et al., *J. Biol. Chem.* 265:6453–6460 (1990).
Behrendt, N. et al., *J. Biol. Chem.* 268:5985–5989 (1993).
Billström et al., *Int. J. Cancer*, 61:542–47 (1995).
Bridges, *Bioorganic & Medicinal Chemistry*, 1:403–410 (1993).
Chamberlin et al., *J. Biol. Chem.*, 270:21062–21067 (1995).
Conese, M. et al. (1995) *Bio. Chem. Hoppe–Seyler* 376, 143–155.
Danø, K. et al., *Adv. Cancer Res.*, 44:139–266 (1985).
Dumler, I. et al., *FEBS Lett.* 322:37–40 (1994).
Ellis, V. et al., *J. Biol. Chem.*, 264:2185–88 (1989).
Fazioli, F. et al., *Trends Pharmacological Sci.*, 15:25–29 (1994).
Geratz et al., *Thrombosis Res.* 24:73–83 (1981).
Goodson, R.J. et al., *Proc Natl Acad Sci USA* 91:7129–7133 (1994).
Hansen et al., *Biochemistry*, 33:4847–64 (1994).
Hansen, A.P. et al., *Biochemistry* 33:15418–15424 (1994).
He, C. et al., *Proc. Natl. Acad. Sci. USA*, 86:2632–36 (1989).
Hunter et al., *Protein Sci.*, 4:2129–37 (1995).
Kellen et al., *Anticancer Res.* 8:1373–76 (1988).
Kobayashi, H. et al., *Int. J. Cancer*, 57:727–33 (1994).
Leszczynski, J.F. et al., *Science* 234:849–855 (1986).
Lougheed et al., *Protein Sci.*, 4:773–80 (1995).
Lu, H. et al., *FEBS Lett.* 380:21–24 (1996).
Magdolen et al., "Systematic Mutational Analysis of the Receptor–binding Region of the Human Urokinase–type Plasminogen Activator", *Eur. J. Biochem.*, 237:743–51 (1996).
Mandriota, S.J. et al., *J. Biol. Chem.*, 270:9709–9716 (1995).
Matrisian, L.M. *Bioessays*, 14:455–63 (1992).
Mazar, A.P. et al., *Fibrinolysis* 6 (Suppl. 1):49–55 (1992).
Mignatti, P. et al., *Cell*, 47:487–98 (1986).
Mignatti, P. et al., *J. Cell Biol.*, 113:1193–1201 (1991).
Min et al., *Cancer Res.*, 56:2428–33 (1996).
Montesano, R. et al., *Proc. Natl. Acad. Sci. USA*, 83:7297–7301 (1986).
Odekon, L.E. et al., *J. Cellul. Physiol.*, 150:258–63 (1992).
Pepper, M.S. et al., *Biochem. Biophys. Res. Comm.*, 181:902–906 (1991).
Rabbani, S.A. et al., *Int. J. Cancer*, 63:840–45 (1995).
Rabbani, S.A. et al., *J. Biol. Chem.*, 267:14151–56 (1992).
Rao, N.K. et al., *J. Clin. Invest.* 96:465–74 (1995).
Rizo, J. et al., *Ann. Rev. Biochem.* 61:387–418 (1992).
Robbiati et al., *Fibrinolysis*, 4:53–60 (1990).
Robbins, K.C. *Meth. Enzymol.*, 19:184–99 (1970).
Ronday et al., *Br. J. Rheum.*, 35:416–423 (1996).
Schnaper, H.W. et al., *J. Cellul. Physiol.* 165:107–118 (1995).
Stoppelli et al., *Proc. Natl. Acad. Sci. USA* 82:4939–43 (1985).
Stratton–Thomas et al., *Protein Engineering* 8:463–70 (1995).
Towle et al., *Cancer Res.*, 53:2553–59 (1993).
Vassalli et al., *FEBS Lett.*, 214:187–191 (1987).
Wang, N. et al., *Am. J. Physiol.* 268:C1062–C1066 (1995).
Werb, Z. et al., *N. Eng. J. Med.*, 296:1017–1023 (1977).
Yang, H. et al., *Fibrinolysis*, 6 *(Suppl. 1)*:31–34, (1992).
Yang, H. et al., *J. Med. Chem.*, 33:2956–61 (1990).
Markus Bürgle et al., "Inhibition of the Interaction of Urokinase–Type Plasminogen Activator (uPA) with its Receptor (uPAR) by Synthetic Peptides", Biological Chemistry, vol. 378, Mar./Apr. 1997, pp 231–237.

* cited by examiner

Primary Examiner—Michael Pak
(74) Attorney, Agent, or Firm—Shmuel Livnat; Venable (57) ABSTRACT

Cyclic peptide compounds having 11 amino acids joined by a linking unit L, such that the linear dimension between the $C^\alpha$ carbon of the first amino acid and the $C^\alpha$ carbon of eleventh amino acid is between about 4 and 12 Ångstrom units; are useful for inhibiting the binding of uPA to the uPAR receptor. Methods for using the cyclic peptide compounds, and compositions containing them, for inhibiting the growth or metastasis of cancerous tumors are also disclosed.

12 Claims, 2 Drawing Sheets

METHOD OF USING CYCLIC PEPTIDES TO INHIBIT BINDING TO UROKINASE-TYPE PLASMINOGEN ACTIVATOR RECEPTOR

This application is a Divisional of application Ser. No. 08/747,915 filed Nov. 12, 1996 and now U.S. Pat. No. 5,942,492.

TECHNICAL FIELD

The present invention relates to certain cyclic peptides that bind to the cell surface receptor for urokinase-type plasminogen activator and, thus, are capable of inhibiting the binding of urokinase-type plasminogen activator to this cell surface receptor. The invention also relates to pharmaceutical compositions containing these peptides and to the use of these peptides to inhibit the binding of urokinase-type plasminogen activator to its cell surface receptor. Effects derived from the inhibition of binding of urokinase-type plasminogen activator to its cell surface receptor include the inhibition of proteolysis; the inhibition of programmed gene expression; the inhibition of cell motility, migration, and morphogenesis; the inhibition of the activation of certain pro-growth factors to the active form of the growth factor; the inhibition of angiogenesis; the inhibition of tumor metastasis; the inhibition of retinal neovascularization in the treatment of certain forms of blindness; and the inhibition of tissue remodeling as a treatment for inflammatory diseases, such as arthritis. The peptides of the invention that are capable of carrying a suitable radioactive, fluorogenic, chromogenic, or chemical label can also be used to quantitate urokinase-type plasminogen activator receptor levels in tissue samples and can be used, therefore, as diagnostic and prognostic tools in all diseases where the receptor plays a pathological role, including those mentioned above.

BACKGROUND OF THE INVENTION

Urokinase-type plasminogen activator (uPA) has been identified as the initiator of a major amplified cascade of extracellular proteolysis. This cascade, when regulated, is vital to certain normal physiological processes but, when dysregulated, is strongly linked to pathological processes, such as cell invasion and metastasis in cancer. Danø et al. *Adv. Cancer Res.*, 44:139–266 (1985). Cells express uPA as an inactive form, pro-uPA or single-chain uPA, which then binds to its receptor, uPAR. This binding event is necessary for activation to two-chain uPA. Ellis et al., *J. Biol. Chem.*, 264:2185–88 (1989). The amino acid sequence for human pro-uPA is as follows:

| Amino Acid | Three-letter Symbol |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

Figure 1:
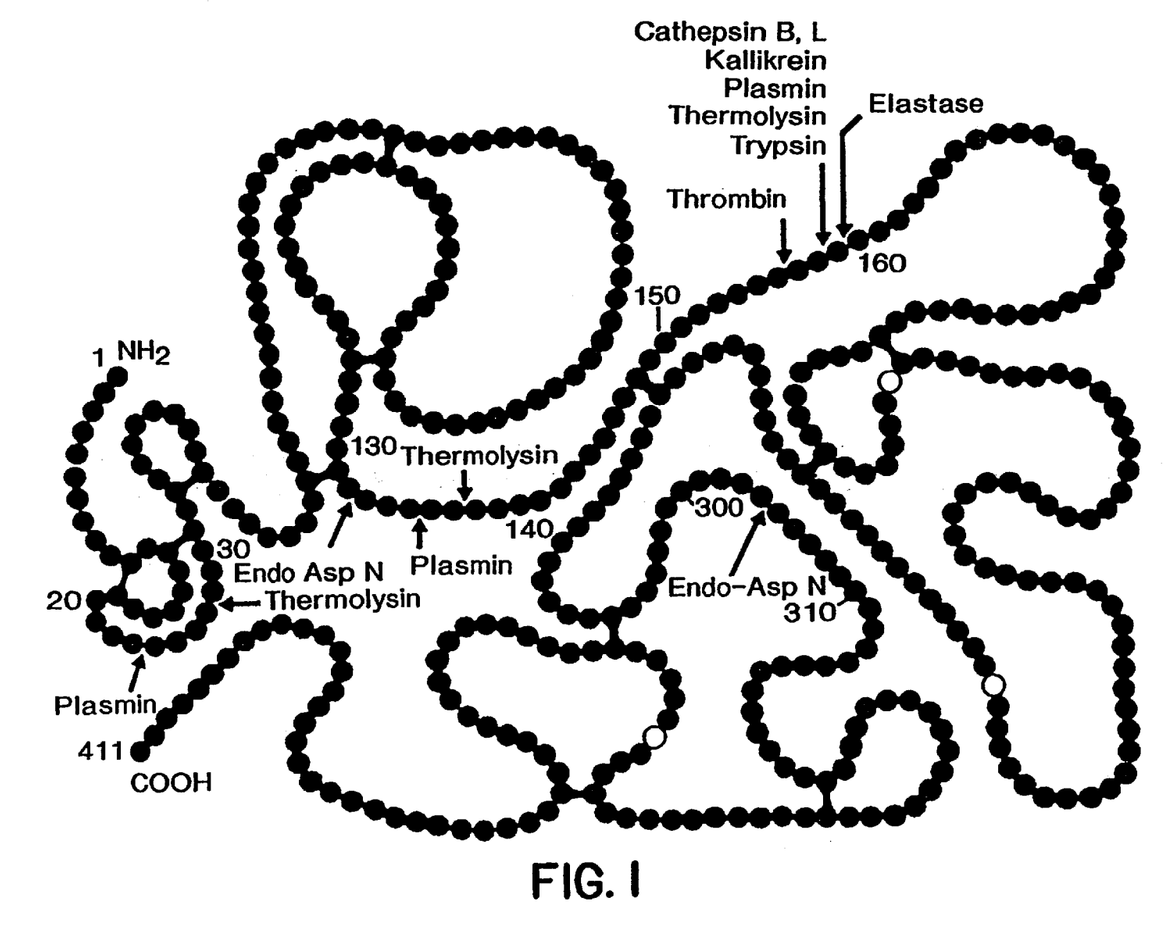
FIG. 1 is a schematic representation of the pro-uPA molecule and its major cleavage sites.

The structure of pro-uPA is shown in FIG. 1.

uPA is a three-domain protein comprising (1) an N-terminal epidermal growth factor-like domain, (2) a kringle domain, and (3) a C-terminal serine protease domain. The receptor for pro-uPA (uPAR) is a multi-domain protein anchored by a glycolipid to the cell membrane, thus ensuring that activation of uPA is a pericellular event. Behrendt . et al., *Biol. Chem. Hoppe-Seyler*, 376.269–79 (1995). uPA activity is confined to the cell surface by plasminogen activator inhibitors (PAI-1 and PAI-2), which bind to and inactivate the bound uPA. This tight control of uPA activity is necessary because uPA acts upon a substrate, plasminogen, that is present at a high concentration in plasma. Robbins, *Meth. Enzymol.*, 19:184–99 (1970). The product of uPA's action upon plasminogen, plasmin, is a powerful broad spectrum protease that not only degrades extracellular matrix proteins directly, but also activates the latent forms of other proteases, including several metaloproteases. Werb et al., *N. Eng. J. Med*, 296:1017–1023 (1977); Mignatti et al., *Cell*, 47:487–98 (1986); He et al., *Proc. Natl. Acad. Sci. USA*, 86:2632–36 (1989); and Matrisian, *Bioessays*, 14:455–63 (1992).

In tumor biology, the link between extracellular proteolysis and angiogenesis is clearly evident. Break-up and dissolution of existing extracellular matrix is necessary in order to create new space for blood vessels to grow into. The processes of proteolysis and angiogenesis are highly coordinated. For example, two pre-eminent angiogenic growth factors, basic fibroblast growth factor and vascular endot-

```
Ser Asn Glu Leu His Gln Val Pro Ser Asn Cys Asp Cys Leu Asn Gly
 1                                  10

Gly Thr Cys Val Ser Asn Lys Tyr Phe Ser Asn Ile His Trp Cys Asn Cys
            20                                  30

Pro Lys Lys Phe Gly Gly Gln His Cys Glu Ile
                        40
```

The sequence of amino acids of pro-uPA are represented above by their standard three-letter abbreviations as follows:

helial growth factor markedly up-regulate the production of uPA. (Montesano et al., *Proc. Natl. Acad Sci. USA,*

83:7297–7301 (1986); Pepper et al., *Biochem. Biophys. Res. Comm.*, 181:902–906 (1991)) and the expression of uPAR by endothelial cells (Mignatti et al., *J. Cell Biol.*, 113:1193–1201 (1991); Mandriota et al., *J. Biol. Chem.*, 270:9709–9716 (1995)). Thus uPA/uPAR has emerged as a new target for developing an anti-metastatic/anti-angiogenic therapy for cancer, where most studies have been conducted (Fazioli et al., *Trends Pharmacological Sci.*, 15:25–29 (1994).

However, the uPA/uPAR interaction goes far beyond localizing proteolysis at the cell surface. Independent of all proteolytic effects, the mere occupation of uPAR by uPA induces, by indirect means, signal transduction events leading to one or more of the following effects: mitogenesis (Rabbani et al., *J. Biol. Chem.*, 267:14151–56 (1992)); expression of the c-fos gene (Dumler et al., *FEBS Lett.* 322:37–40 (1994)); cysteine- and metalloprotease expression by macrophages (Rao et al., *J. Clin. Invest.* 96:465–74 (1995)): transfer of mechanical force leading to increased cytoskeletal stiffness (Wang et al., *Am. J. Physiol.*, 268:C1062–C1066 (1995)); endothelial cell migration (Odekon et al., *J. Cellul. Physiol.*, 150:258–63 (1992)); endothelial cell morphogenesis into tubular structures (Schnaper et al., *J. Cellul. Physiol.* 165:107–118 (1995)); and endothelial cell deformability and motility (Lu et al., *FEBS Lett*. 380:21–24 (1996)). All of these phenomena are blocked by blocking the access of uPA to uPAR. An antagonist of uPAR that prevented the binding of uPA would thus interfere with proteolytic activity by preempting uPA activation and, further, would greatly diminish uPAR's capacity for signal transduction.

The anti-angiogenic effects accompanying uPAR antagonism (Min et al., *Cancer Res.*, 56:2428–33 (1996)) should allow a uPAR antagonist to play a role in other diseases characterized by inappropriate angiogenesis, e.g. ocular angiogenesis leading to blindness. Furthermore, it is likely that a uPAR antagonist would also play a therapeutic role in inflammatory diseases, for example, rheumatoid arthritis. (Ronday et al., Br. J. Rheum., 35:416–423 (1996).

One approach to drug therapy is to target uPA itself at its catalytic serine protease domain. Yang et al., *Fibrinolysis*, 6 (Suppl. 1):31–34, (1992). Amiloride (Vassalli et al., *FEBS Lett.*, 214:187–191 (1987); and Kellen et al., *Anticancer Res*. 8:1373–76 (1988)) and p-aminobenzamidine (Geratz et al., *Thrombosis Res*. 24:73–83 (1981); and Billström et al., *Int. J. Cancer*, 61:542–47 (1995)) are competitive inhibitors of this site and have anti-metastatic activity in vivo. Selective inhibition of uPA as compared with other serine proteases, was evident in phenylguanidines (Yang et al., *J. Med Chem.*, 33:2956–61 (1990)) and, even more so, in benzo[b]thiophene-2-carboxamidines (Bridges, Bioorganic & Medicinal Chemistry, 1:403–410 (1993); Towle et al., *Cancer Res.*, 53:2553–59 (1993); and Rabbani et al., *Int. J. Cancer*, 63:840–45 (1995)).

Towards defining the binding epitope for the uPA-uPAR interaction, it was first shown that the amino terminal fragment of uPA (residues 1–135) that lacked the serine protease domain, sufficed for high affinity, sub-nanomolar binding. (Stoppelli et al., *Proc. Natl. Acad. Sci. USA* 82:4939–43 (1985). Further work showed that the growth factor domain alone (residues 1–48) conferred this binding. (Robbiati et al., *Fibrinolysis*, 4:53–60 (1990); and Stratton-Thomas et al., *Protein Engineering* 8:463–70 (1995).) Danø et al., in WO 90/12091 published Oct. 18, 1990, discloses that the binding of uPA to uPAR could be prevented by administering a substance comprising a sequence identical or substantially identical to a uPAR binding site of uPA amino residues 12–32. WO 94/28145, by Rosenberg and Stratton-Thomas, Dec. 8, 1994, discloses the preparation and use of de-fucosylated $HuPA_{1-48}$ that prevents uPA binding to uPAR.

Earlier studies with peptide fragments within the growth factor domain had showed that residues 20–30 conferred the specificity of binding, but that residues 13–19 were needed in addition for residues 20–30 to attain the proper binding conformation. Specifically, the peptide $[Ala^{19}]uPA-(12-32)$, which contains two cysteines (the third cysteine being replaced by Ala to avoid undesired disulfide bond formations), in its open chain form prevented uPA binding to uPAR with an $IC_{50}$ of 100 nM. In its oxidized cyclic form, having an intrachain disulfide bond between $Cys^{13}$ and $Cys^{31}$, the peptide prevented binding with an $IC_{50}$ of 40 nM. It was proposed that residues 13–19 might act indirectly to provide a scaffold that would help residues 20–30 attain the correct binding conformation. Appella et al., *J. Biol. Chem.*, 262:4437–40 (1987).

These results were partially confirmed when it was reported that, while the linear peptide 20–30 inhibited the binding of uPA to uPAR with an $IC_{50}$ of 1,000 nM, the longer peptide 17–34 was significantly more potent, having an $IC_{50}$ of 100 nM. It was also shown that the corresponding longer peptide (17–34) derived from the mouse sequence inhibited spontaneous metastasis of a murine Lewis Lung carcinoma in mice, whereas the corresponding linear shorter peptide (20–30) had no effect. Kobayashi et al., *Int. J. Cancer*, 57:727–33 (1994). WO 94/28014 by Rosenberg and Doyle, Dec. 8, 1994 discloses the preparation and use of 25 random peptides displayed on bacteriophage which competed with the N-terminal fragment of uPA for binding to uPAR with $IC_{50}$ values of 15 nM to >50 $\mu$M.

Figure 2:
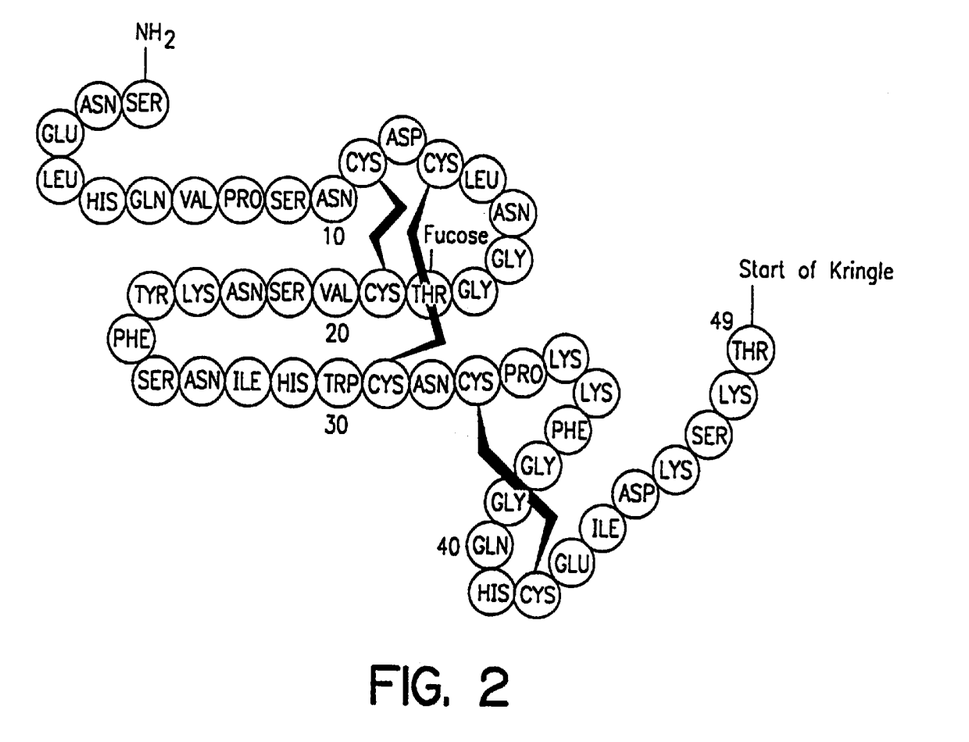
FIG. 2 shows the NH-terminal growth factor domain of human uPA.

Most recently, Magdolen et al., "Systematic Mutational Analysis of the Receptor-binding Region of the Human Urokinase-type Plasminogen Activator", *Eur. J. Biochem.*, 237:743–51 (1996), describes alanine-scanning mutagenesis of the binding loop of the amino-terminal fragment of uPA with the finding that Asn22, Lys23, Tyr24, Phe25, Ile28 and Trp30 are important side chains that should be kept. Further, Magdolen et al., citing Hansen et al., *Biochemistry*, 33:4847–64 (1994), disclose that the region between Thr 18 and Asn32 consists of a flexible, seven-residue omega loop that is forced into a ring-like structure. Although Cys19 and Cys31 are in close proximity to each other (0.61 nm), they do not form a disulfide bond with each other. Instead Cys19 forms a disulfide bond with Cys 11, and Cys31 forms a bond with Cys 13. See FIG. 2. Accordingly, the uPAR binding site on uPA does not form a simple, small ring structure.

Some scientists have explored the possibility of cyclizing the one or more of the growth factor domains of peptide analogues to increase their competitive binding activity, but not with any great success without at least adding some other constraining-type modifications of the structure. For example, in Chamberlin et al., *J. Biol. Chem.*, 270:21062–21067 (1995), peptides constrained by the introduction of an intramolecular disulfide bond also required the substitution of another entity for proline in the peptide loop to achieve any significant activity. Lougheed et al., *Protein Sci.*, 4: 773–80 (1995) found that peptides from the fifth EGF-like domain of thrombomodulin had very weak biological activity that increased marginally (two-fold) by cyclization. The additional presence of a "tail" of amino acids and the deletion of one of the amino acids were both found necessary and, even then, the best peptide was only weakly active (text of micromolar range). Thus, cyclization per se conferred no significant activity. Further, others working in the thrombomodulin field have found that the number of crossing disulfide bonds in the fifth EGF-like domain is inversely, rather than directly, related to inhibitory potency. Hunter et al., *Protein Sci.*, 4:2129–37 (1995).

It has now been found by the present inventors that novel cyclic structures derived from the peptide fragment 20–30, in which residue 20 is covalently bonded to residue 30, do exhibit the ability to bind to uPAR and are also antagonists of the binding of uPA to uPAR. These peptides are shorter than either [Ala$^{19}$]uPA-(12–32) (Appella et al., supra.) or uPA17–34 (Kobayashi et al., supra.), but bind almost as effectively. In contradiction of what was hitherto thought, it has been discovered that the eight amino acids N-terminal to Val20 in [Ala$^{19}$]uPA-(12–32) and the four amino acids CO-terminal to Trp30 in uPA17–34 are not necessary for high binding affinity. While not wishing to be bound by any particular theory, it now appears that the minimal binding epitope in urokinase-type plasminogen activator, which is needed for binding to its receptor, is a loop of only eleven amino acids.

DISCLOSURE OF THE INVENTION

The invention is a cyclic peptide compound of Formula 1 or Formula 2

Formula 1

Formula 2 wherein, in Formula 1, all of $X^1$ through $X^{11}$ represent L-series amino acids and, in Formula 2, all of $X^1$ through $X^{11}$ represent D-series amino acids;

$X^1$ is Val, Pro, or Ala;

$X^2$ is Ser or Ala;

$X^3$ is Asn or Gln;

$X^4$ is Lys or His;

$X^5$ is Tyr, Trp, Phe, substituted Phe, di-substituted Phe, homophenylalanine, β-(3-pyridyl)alanine, β-(2-thienyl)alanine, β-(1-naphthyl)alanine, or β-(2-naphthyl)alanine;

$X^6$ is Tyr, Trp, Phe, substituted Phe, di-substituted Phe, homophenylalanine, β-(3-pyridyl)alanine, β-(2-thienyl)alanine, β-(1-naphthyl)alanine, or β-(2-naphthyl)alanine;

$X^7$ is Ser or Ala;

$X^8$ is Asn or Ala;

$X^9$ is Ile, Leu, or Val;

$X^{10}$ is His or Ala;

$X^{11}$ is Tyr, Trp, Phe, substituted Phe, di-substituted Phe, homophenylalanine, β-(3-pyridyl)alanine, β-(2-thienyl)alanine, β-(1-naphthyl)alanine, or β(2-naphthyl)alanine; and L is a linking unit, such that when $X^1$ and $X^{11}$ are linked, the linear dimension between the $C^\alpha$ carbon of amino acid $X^1$ and the $C^\alpha$ carbon of amino acid $X^{11}$ is between about 4 and 12 Ångstrom units;

with the proviso that, when said compound is of Formula 1, L does not comprise two cysteine units linked by a disulfide bond.

In other embodiments, the compounds of the invention are used in methods and therapeutic compositions to inhibit the binding of uPA to uPAR, particularly in the treatment of cancer.

DETAILED DESCRIPTION OF THE INVENTION

The cyclic peptide compounds of the invention can be of either Formula 1 or the corresponding retro-inverso cyclic peptide compounds of Formula 2. When the cyclic peptide compounds of the invention are of Formula 1, all of $X^1$ through $X^{11}$ represent L-series natural amino acids. On the other hand, when the compounds of the invention are of Formula 2, all of $X^1$ through $X^{11}$ represent D-series non-natural amino acids. Whether of Formula 1 or Formula 2, however, when any one of $X^5$, $X^6$ or $X^{11}$ is a substituted or disubstituted phenylalanine, the substituent is halo, such as 4-fluoro, 4-chloro, 4-bromo, or 3,4-dichloro; lower alkyl, such as methyl, ethyl, isopropyl, tertiary butyl or n-pentyl; nitro; or the like.

The linker moiety L in the compounds of the invention forms a bridge between $X^{11}$ and $X^1$, thus cyclizing the compound. The linker L can be almost any divalent group which would set the linear dimension between the $C^\alpha$ carbon of amino acid $X^1$ and the $C^\alpha$ carbon of amino acid $X^{11}$ between about 4 and 12 Ångstrom units, preferably between about 5 and 10 Ångstrom units and, even more preferably, between about 6 and 8 Ångstrom units.

Compounds of Formula 1

In Formula 1, the amide bond, CO—NH, which links $X^1$ to $X^2$, is such that the C=O moiety is from the amino acid $X^1$ and the NH moiety is from the amino acid $X^2$. The same arrangement applies to the link between $X^2$ and $X^3$, and so on. In other words, the peptide has $X^1$ as its N-terminus and $X^{11}$ as its C-terminus.

It should be noted, however, that L cannot comprise two cysteine units linked by a disulfide bond, be it unsubstituted, substituted at its N-terminus with a group $R^1$, substituted at its C-terminus with a group $R^2$, or modified at both N— and C-termini, respectively, with $R^1$ and $R^2$, where $R^1$ is acetyl and $R^2$ is amino such that the C-terminus is a primary carboxamide. Specific examples of such excluded L groups include:

—CO—CH(NH$_2$)—CH$_2$—S—S—CH$_2$—CH(COOH)—NH—;

—CO—CH(NHR$^1$)—CH$_2$—S—S—CH$_2$—CH(COOH)—NH—,

—CO—CH(NH₂)—CH—S—S—CH₂—CH(COR²)—NH—, and

—CO—CH(NHR¹)—CH₂—S—S—CH₂—CH(COR²)—NH—.

To prepare the compounds of Formula 1, L is chosen so as to provide, at one of its termini, a functional group that can be chemically bonded to the carbon of the α-carboxyl group of the amino acid $X^{11}$ and, at its other terminus, a functional group that can be chemically bonded to the α-amino nitrogen atom of the amino acid $X^1$.

Alternatively, the linear peptide $X^1$-$X^2$-$X^3$-$X^4$-$X^5$-$X^6$-$X^7$-$X^8$-$X^9$-$X^{10}$-$X^{11}$ can be synthesized with an extension at its $X^{11}$ terminus comprising a portion of the final linker group, i.e., $L_b$, and later, after synthesis of the desired peptide chain, the $X^1$ terminus can be extended with a group $L_a$, to give the compound $L_a$-$X^1$-$X^2$-$X^3$-$X^4$-$X^5$-$X^6$-$X^7$-$X^8$-$X^9$-$X^{10}$-$X^{11}$-$L_b$. The free ends of $L_a$ and $L_b$ can then be chemically bonded to each other. In this way, the linker L can be formed during the cyclization step from pre-attached fragments $L_a$ and $L_b$. In the examples given below for L, the direction of L, reading left to right, is from to $X^1$ to $X^{11}$, i.e., the CO-terminus of L is connected to $X^1$, and the NH— terminus of L is connected to $X^{11}$.

Typical examples of useful L groups for Formula 1 include the following:

—CO—CH₂—CH₂—S—CH₂—CH(COOH)—NH—;

—CO—CH₂—CH₂—CH₂—CH₂—S—CH—CH(COOH—NH—,

—CO—CH(NH₂)—CH₂—S—CH₂—CH₂—CH₂—NH—;

—CO—CH₂—CH₂—S—CH₂—CH₂—CH₂—NH—;

—CO—CH₂—CH₂—CH₂—CH₂—CH₂—CH₂—NH—;

—CO—CH₂—CH₂—S—CH₂—CH₂—CH(COOH)—NH—;

—CO—CH₂—CH₂—CH₂—CH₂—CH₂—CH(COOH)—NH—,

—CO—CH₂—S—CH₂—CH(COOH)—NH—,

—CO—CH₂—S—CH₂CH₂—CH(COOH)—NH—; and

—CO—CH₂—meta-phenylene—CH₂—NH—.

When L contains a cysteine or a homocysteine residue, the configuration of the enantiomeric center of such a residue can be either L— or D—.

Compounds of Formula 2 (Retro-inverso Compounds)

When the cyclic peptide compound of the invention is of Formula 2, the amino acids $X^1$–$X^{11}$ are non-natural, "D-series" peptides having an enantiomeric configuration opposite to that the of L-series natural amino acids described above for Formula 1. In Formula 2, the amide bond CO—NH, which links $X^{11}$ to $X^{10}$, is such that the C=O moiety is from the amino acid $X^{11}$ and the NH moiety is from the amino acid $X^{10}$. The same arrangement applies to the link between $X^{10}$ and $X^9$ and so on. In other words, the peptide has $X^{11}$ as its N-terminus and $X^1$ as its C-terminus.

In the above structure of Formula 2, the moiety L is chosen so as to provide, at one of its termini, a functional group that can be chemically bonded to the α-amino nitrogen atom of the $X^{11}$ residue, rather than the α-carboxyl group and, at its other terminus, a functional group that can be chemically bonded to the carbon of the α-carboxyl group of the of the amino acid $X^1$, rather than the α-amino nitrogen atom, as described above.

Also as described above, the linear peptide $X^1$-$X^2$-$X^3$-$X^4$-$X^5$-$X^6$-$X^7$-$X^8$-$X^9$-$X^{10}$-$X^{11}$ can be synthesized at its $X^1$ terminus with a group $L_b$ and, at its $X^{11}$ terminus, with a group $L_a$ to give the compound $L_b$-$X^1$-$X^2$-$X^3$-$X^4$-$X^5$-$X^6$-$X^7$-$X^8$-$X^9$-$X^{10}$-$X^{11}$-$L_a$, such that the free ends of $L_a$ and $L_b$ can be chemically bonded to form the cyclic retro-inverso compounds of the invention.

In the examples given below for L, the direction of L, reading left to right, is from to $X^1$ to $X^{11}$, that is, the NH-terminus of L is covalently bonded to $X^1$, and the CO terminus of L is connected to $X^{11}$. When these linkers contain a cysteine or a homocysteine residue, the configuration of the enantiomeric center of such a residue can be either the D- or L- form.

Examples of useful L groups for the retro-inverso peptides of Formula 2 include:

—NH—CH(COOH)—CH₂—S—CH₂—CH₂—CH₂—CO—;

—NH—CH(COOH)—CH₂—S—CH₂—CH₂—CH₂—CH₂—CO—;

—NH—CH₂—CH₂—CH₂S—CH₂—(NH₂)—CO—;

—NH—CH₂—CH₂—CH₂—S—CH₂—CH₂—CO—;

—NH—CH₂—CH₂—CH₂—CH₂—CH₂—CH₂—CO—;

—NH—CH(COOH)—CH₂—CH—S—CH₂—CH₂—CO—;

—NH—CH(COOH)—CH₂—CH₂—CH₂—CH₂—CH₂—CO—;

—NH—CH(COOH)—CH₂—S—CH₂—CO—;

—NH—CH(COOH)—CH₂—CH₂—S—CH₂—CO—; and

—NH—CH₂—meta-phenylene—CH₂—CO—.

General Chemical Synthetic Procedures

When the peptides of the invention are not prepared using recombinant DNA technology, they are preferably prepared using solid-phase synthesis, such as that generally described by Merrifield, *J. Amer. Chem. Soc.*, 85:2149–54 (1963), although other equivalent chemical syntheses known in the art are also useful. Solid-phase peptide synthesis may be initiated from the C-terminus of the peptide by coupling a protected α-amino acid to a suitable resin. Such a starting material can be prepared by attaching an α-amino-protected amino acid by an ester linkage to a chloromethylated resin or to a hydroxymethyl resin, or by an amide bond to a BHA resin or MBHA resin.

The preparation of the hydroxymethyl resin is described by Bodansky et al., *Chem. Ind*, 38:1597–98 (1966). Chloromethylated resins are commercially available from Bio-Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, 1–6. BHA and MBHA resin supports are commercially available and are generally used only when the desired polypeptide being synthesized has an unsubstituted amide at the C-terminus.

The amino acids $X^1$ through $X^{11}$ can be coupled to the growing peptide chain using techniques well known in the art for the formation of peptide bonds. For example, one method involves converting the amino acid to a derivative that will render the carboxyl group of the amino acid more susceptible to reaction with the free N-terminal amino group of the growing peptide chain. Specifically, the C-terminal of the protected amino acid can be converted to a mixed anhydride by the reaction of the C-terminal with ethyl. chloroformate, phenyl chloroformate, sec-butyl chloroformate, isobutyl chloroformate, or pivaloyl chloride or the like acid chlorides. Alternatively, the C-terminal of the amino acid can be converted to an active ester, such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves the use of a suitable coupling agent, such as N,N'dicyclohexylcarbodiimide or N,N'-diisopropylcarbodiirnide. Other appropriate coupling agents, apparent to those skilled in the art, are disclosed in Gross et al., *The Peptides: Analysis, Structure, Biology*, Vol. I., "Major Methods of Peptide Bond Formation" (Academic Press 1979), the disclosure of which is hereby incorporated by reference.

It will be recognized that the α-amino group of each amino acid employed in the peptide synthesis must be protected during the coupling reaction to prevent side reactions involving their active α-amino function. It should also be recognized that certain amino acids contain reactive side-chain functional groups (e.g. suffhydryl, amino, carboxyl, and hydroxyl) and that such functional groups must also be protected with suitable protecting groups to prevent a chemical reaction from occuning at either (1) the α-amino group site or (2) a reactive side chain site during both the initial and subsequent coupling steps.

In the selection of a particular protecting group to be used in synthesizing the peptides, the following general rules are typically followed. Specifically, an α-amino protecting group (a) should render the α-amino function inert under the conditions employed in the coupling reaction, (b) should be readily removable after the coupling reaction under conditions that will not remove side-chain protecting groups and will not alter the structure of the peptide fragment, and (c) should substantially reduce the possibility of racemization upon activation, immediately prior to coupling.

On the other hand, a side-chain protecting group (a) should render the side chain functional group inert under the conditions employed in the coupling reaction, (b) should be stable under the conditions employed in removing the α-amino protecting group, and (c) should be readily removable from the desired fully-assembled peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups, such as triphenylmethyl and 2-(p-biphenyl)isopropyloxycarbonyl, are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl, are less labile and require moderately strong acids for their removal, such as trifluoroacetic, hydrochloric, or boron trifluoride in acetic acid. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require even stronger acids, such as hydrogen fluoride, hydrogen bromide, or boron trifluoroacetate in trifluoroacetic acid, for their removal. Suitable protecting groups, known in the art are described in Gross et al., *The Peptides: Analysis, Structure, Biology,*. Vol. 3: "Protection of Functional Groups in Peptide Synthesis" (Academic Press 1981).

Among the classes of amino acid protecting groups useful for protecting the α-amino group or for protecting a side chain group are included the following.

(1) For an α-amino group, three typical classes of protecting groups are: (a) aromatic urethane-type protecting groups, such as fluorenylmethyloxycarbonyl (FMOC), CBZ, and substituted CBZ, such as, e.g., p-chlorobenzyloxycarbonyl, p-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenyl)-isopropyloxycarbonyl, allyloxycarbonyl and the like; and (c) cycloalkyl urethane-type protecting groups, such as cyclopentyloxycarbonyl, adamantyloxycarbonyl, and cyclohexyloxycarbonyl. The preferred α-amino protecting groups are BOC and FMOC.

(2) For the side chain amino group present in Lys, protection may be by any of the groups mentioned above in (1) such as BOC, 2-chlorobenzyloxycarbonyl and the like.

(3) For the guanidino group of Arg, protection may be provided by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC groups.

(4) For the hydroxyl group of Ser, Thr, or Tyr, protection may be, for example, by t-butyl; benzyl (BZL); or substituted BZL, such as p-methoxybenzyl, p-nitrobenzyl, p-chlorobenzyl, o-chlorobenzyl, and 2,6-dichlorobenzyl.

(5) For the carboxyl group of Asp or Glu, protection may be, for example, by esterification using such groups as BZL, t-butyl, cyclohexyl, cyclopentyl, and the like.

(6) For the imidazole nitrogen of His, the benzyloxymethyl (BOM) or tosyl moiety is suitably employed as a protecting group.

(7) For the phenolic hydroxyl group of Tyr, a protecting group such as tetrahydropyranyl, tert-butyl, trityl, BZL, chlorobenzyl, 4-bromobenzyl, and 2,6-dichlorobenzyl are suitably employed. The preferred protecting group is bromobenzyloxycarbonyl.

(8) For the side chain amino group of Asn or Gin, xanthyl (Xan) is preferably employed.

(9) For Met, the amino acid is preferably left unprotected.

(10) For the thio group of Cys, p-methoxybenzyl is typically employed.

The first C-terminal amino acid of the growing peptide chain, e.g., Lys, is typically protected at the N-amino position by an appropriately selected protecting group such as BOC. The BOC-Lys-(2-chlorobenzyloxycarbonyl)—OH group can be first coupled to a benzylhydrylamine resin using isopropylcarbodiimide at about 25° C. for two hours with stirring or to a chloromethylated resin according to the procedure set forth in Horiki et al., *Chemistry Letters*, 165–168 (1978). Following the coupling of the BOC-protected amino acid to the resin support, the α-amino protecting group is usually removed, typically by using trifluoroacetic acid (TFA) in methylene chloride or TFA alone. The α-amino group de-protection reaction can occur over a wide range of temperatures, but is usually carried out at a temperature between about 0° C. and room temperature.

Other standard α-amino group de-protecting reagents, such as HCl in dioxane, and conditions for the removal of specific α-amino protecting groups are within the skill of those working in the art, such as those described in Lübke et al., *Chemie und Biochemie der Aminosaüren, Peptide und Proteine I*, Chapter II-1, 102–117 (Georg Thieme Verlag Stuttgart 1975), which is hereby incorporated by reference.

Following the removal of the α-amino protecting group, the unprotected α-amino group, generally still side-chain protected, can be coupled in a stepwise manner in the intended sequence.

An alternative to the stepwise approach is the fragment condensation method in which pre-formed peptides of short length, each representing part of the desired sequence, are coupled to a growing chain of amino acids bound to a solid phase support. For the stepwise approach, a particularly suitable coupling reagent is N,N'-dicyclohexyl-carbodiimide or diisopropylcarbodiimide. Also, for the fragment approach, the selection of the coupling reagent, as well as the choice of the fragmentation pattern needed to couple fragments of the desired nature and size are important for success and are known to those skilled in the art.

Each protected amino acid or amino acid sequence is usually introduced into the solid-phase reactor in amounts in excess of stoichiometric quantities, and the coupling is suitably carried out in an organic solvent, such as dimethylformamide (DMF), $CH_2Cl_2$ or mixtures thereof If incomplete coupling occurs, the coupling procedure is customarily repeated before removal of the N-amino protecting group in preparation for coupling to the next amino acid. Following the removal of the α-amino protecting group, the remaining α-amino and side-chain-protected amino acids can be coupled in a stepwise manner in the intended sequence. The success of the coupling reaction at each stage of the synthesis may be monitored. A preferred method of monitoring the synthesis is by the ninhydrin reaction, as described by Kaiser et al., *Anal. Biochem.*, 34:595 (1970). The coupling reactions can also be performed automatically using well-known commercial methods and devices, for example, a Beckman 990 Peptide Synthesizer.

Upon completion of the desired peptide sequence, the protected peptide must be cleaved from the resin support, and all protecting groups must be removed. The cleavage reaction and removal of the protecting groups is suitably accomplished concomitantly or consecutively with de-protection reactions. When the bond anchoring the peptide to the resin is an ester bond, it can be cleaved by any reagent that is capable of breaking an ester linkage and of penetrating the resin matrix. One especially useful method is by treatment with liquid anhydrous hydrogen fluoride. This reagent will usually not only cleave the peptide from the resin, but will also remove all acid-labile protecting groups and, thus, will directly provide the fully de-protected peptide. When additional protecting groups that are not acid-labile are present, additional de-protection steps must be carried out. These steps can be performed either before or after the hydrogen fluoride treatment described above, according to specific needs and circumstances.

When a chloromethylated resin is used, the hydrogen fluoride cleavage/de-protection treatment generally results in the formation of the free peptide acids. When a benzhydrylamine resin is used, the hydrogen fluoride treatment generally results in the free peptide amides. Reaction with hydrogen fluoride in the presence of anisole and dimethylsulfide at 0° C. for one hour will typically remove the side-chain protecting groups and, concomitantly, release the peptide from the resin.

When it is desired to cleave the peptide without removing protecting groups, the protected peptide-resin can be subjected to methanolysis, thus yielding a protected peptide in which the C-terminal carboxyl group is methylated. This methyl ester can be subsequently hydrolyzed under mild alkaline conditions to give the free C-terminal carboxyl group. The protecting groups on the peptide chain can then be removed by treatment with a strong acid, such as liquid hydrogen fluoride. A particularly useful technique for methanolysis is that of Moore et al., *Peptides, Proc. Fifth Amer. Pept. Symp.*, 518–521 (Goodman et al., eds., 1977), in which the protected peptide-resin is treated with methanol and potassium cyanide in the presence of a crown ether.

Other methods for cleaving a protected peptide from the resin when a chloromethylated resin is employed include (1) ammonalysis and (2) hydrazinolysis. If desired, the resulting C-terminal amide or hydrazide can be hydrolyzed to the free C-terminal carboxyl moiety, and the protecting groups can be removed conventionally. The protecting group present on the N-terminal α-amino group may be removed either before, or after, the protected peptide is cleaved from the support.

Purification of the polypeptides of the invention is typically achieved using chromatographic techniques, such as preparative HPLC (including reverse phase HPLC), gel permeation, ion exchange, partition chromatography, affinity chromatography (including monoclonal antibody columns), and the like, or other conventional techniques such as countercurrent distribution or the like.

The compounds of the invention can be easily tested for their ability to inhibit the binding of pro-uPA to uPAR in a competitive ligand-binding assay. The assay is preferably a solid phase immunoassay that uses the recombinant soluble human urokinase receptor (uPAR) derived from Chinese hamster ovary cells coated onto the walls of test wells to act as capture molecules. The compound being tested competes with pro-uPA for the binding site on uPAR. The amount of pro-uPA that binds to the uPAR on the walls of the test wells can be detected with a biotinylated monoclonal anti-uPA antibody that is, in turn, recognized by streptavidin-horse radish peroxidase. The addition of perborate and 3,3',5,5'-tetramethylbenzidine ("TMB") as a substrate allows the peroxidase to generate a blue-colored product, thus providing a colorimetric signal. The sensitivity of the assay is preferably increased even further by adding sulfuric acid to the test solution, which provides a yellow color that can be easily read out.

In general, the greater the binding of the test compound to uPAR, the greater the exclusion of pro-uPA from binding, and the smaller will be the generated optical signal. The specificity of this capture-type assay is inherent in the purity of the uPAR being used, which itself may be tested by SDS-PAGE, non-reducing Western blot analysis (clean, single band at 46 kD, the known molecular weight of intact uPAR).

The detection antibody in the assay recognizes an epitope within the kringle domain of uPA and, thus, is suitable for measuring the competitive binding of polypeptides that lack the kringle domain, such as the growth factor domain of uPA or peptide derivatives representing a part of the growth factor domain, for example, the compounds of the invention. This assay has been validated against three different forms of uPA: (1) pro-uPA, also known as single-chain uPA; (2) high molecular-weight uPA, also known as two-chain uPA, and (3) low molecular-weight uPA.

A typical assay procedure is as follows:
uPAR is coated onto microtest wells in 96-well plates 0.8 nM (160 ng/mL) pro-uPA is incubated with serially diluted concentrations of the test compound. Both pro-uPA and the compound being tested are diluted in phosphate-buffered saline (PBS) with 0.1% Triton X-100 and 1.0% bovine serum albumin (pH 7.4). The total volume per well of pro-uPA/test compound mixture is 50 µL, and ligands are allowed to bind approximately 16 hours overnight at 4° C. The wells are washed four times with saline wash buffer (100 mM trisodium phosphate, 150 mM sodium chloride, pH 7.4, containing 1% Triton X-100, and 0.025% sodium azide). The detection antibody solution (50 µL) is added, and the mixture is kept at room temperature for one hour. The wells are washed with wash buffer.

Streptavidin-horse radish peroxidase (50 µL) is next added and incubated for one hour at room temperature. The wells are again washed with wash buffer.

Finally, the peroxidase substrate TUB (50 µL) and perborate are added and allowed to react for 20 minutes to generate a blue color. Sulfuric acid (0.5 M, 50 µL) is added to yield a yellow color. The absorbance of the yellow color is then read out at 450 nanometers on an MRX microplate reader made by Dynatech Laboratories. Each test compound is assayed in triplicate at five different concentrations.

The inhibition of binding of pro-uPA to uPAR is usually dose-related, such that-the concentration of the test compound necessary to produce a 50% inhibition of binding (the $IC_{50}$ value) is easily determined. In general, the compounds of the invention have $IC_{50}$ values of less than about $10^{-5}$ molar, i.e., less than about 10 µM. Preferably, the compounds of the invention have $IC_{50}$ values of less than about $10^{-6}$ molar, i.e., less than about 1 µM and, even more preferably, less than about $10^{-7}$ molar.

Administration and Use

The cyclic peptide compounds of the invention that may be employed in the pharmaceutical compositions of the invention include all of those compounds described above, as well as the pharmaceutically acceptable salts of these compounds. Pharmaceutically acceptable acid addition salts of the compounds of the invention containing a basic group are formed where appropriate with strong or moderately strong, non-toxic, organic or inorganic acids in the presence of a basic amine by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

As stated above, the compounds of the invention possess the ability to inhibit uPA formation, a property that may express itself in the form of anti-tumor activity. A compound of the invention may be active per se, or it may be a pro-drug that is converted in vivo to an active compound.

The compounds of the invention, as well as the pharmaceutically acceptable salts thereof, may be incorporated into convenient dosage forms, such as capsules, tablets or injectable preparations. Solid or liquid pharmaceutically acceptable carriers may be employed. Preferably, the compounds of the invention are administered systemically, e.g., by injection. When used, injection may be intravenous, subcutaneous, intramuscular, or even intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of a pharmaceutical chemist involving such steps as mixing, granulating and compressing, when necessary for tablet forms, or mixing, filling and dissolving the ingredients, as appropriate, to give the desired products for oral, parenteral, topical, transdermal, intravaginal, intranasal, intrabronchial, intraocular, intraaural and rectal administration. Of course, these compositions may also contain minor amounts of nontoxic auxiliary substances such as wetting or emulsifying agents, pH buffering agents and so forth.

The compositions of the invention may further comprise one or more other compounds that are anti-tumor agents, such as mitotic inhibitors, e.g., vinblastine; alkylating agents, e.g., methotrexate, pritrexim or trimetrexate); antimetabolites, e.g., 5-fluorouracil and cytosine arabinoside; intercalating antibiotics, e.g., adriamycin and bleomycin); enzymes, e.g., asparaginase; topoisomerase inhibitors, e.g., etoposide; or biological response modifiers, e.g., interferon.

The composition of the invention may also comprise one or more other compounds, including antibacterial, antifungal, anti-parasitic, anti-viral, anti-psoriatic and anti-coccidial agents. Exemplary antibacterial agents include, for example, sulfonamides such as sulfamethoxazole, sulfadiazine, sulfameter or sulfadoxine; DHFR inhibitors such as trimethoprim, bromodiaprim or trimetrexate; penicillins; cephalosporins; aminoglycosides; bacteriostatic inhibitors of protein synthesis; the quinolonecarboxylic acids and their fused isothiazole analogs; and the like.

Another aspect of the invention relates to a therapeutic process preventing the binding of uPA to uPAR, which process comprises administering to a vertebrate host, such as a mammal or bird, an amount effective to inhibit the binding of uPA to uPAR according to the present invention. The compounds of the invention are particularly useful in the treatment of mammalian hosts, such as human hosts and other animal hosts likely to be provided with a veterinarian's care. Further, the peptides of the invention that are capable of carrying a suitable radioactive fluorogenic, chromogenic, or chemical label can also be used to quantitate uPAR levels in tissue samples and has use, therefore, in diseases where the receptor plays a pathological role.

Any of the cyclic peptide compounds described above, or pharmaceutically acceptable salts thereof, may be used in the therapeutic process of the invention. The compounds may be administered in the therapeutic process of the invention in the form of a pharmaceutically acceptable composition comprising a diluent or carrier, such as those described above. Doses of the compounds preferably include pharmaceutical dosage units comprising an efficacious quantity of active compound. By an efficacious quantity is meant a quantity sufficient to inhibit the binding of uPA to uPAR and derive the beneficial effects therefrom through administration of one or more of the pharmaceutical dosage units.

The quantity of compound to be administered depends on the choice of active ingredient, the conditions to be treated, the mode of administration, the individual subject, and the judgment of the practitioner. Depending on the specificity of the preparation, smaller or larger doses may be needed. An exemplary daily dosage unit for a vertebrate host comprises an amount of up to about 5,000 mg of active compound per square meter of the body area of the vertebrate host. Dosages in the range of about 0.05–10 mg/kg are suggested for systemic administration. Dosages in the range of about 0.01–20% concentration of active ingredient, preferably 1–5%, are suggested for topical administration. A total daily dosage in the range of about 10–300 mg is suggested for oral administration. The foregoing ranges are, however, merely suggestive, as the number of variables in regard to an individual treatment regime is large, and considerable excursions from these recommended values are expected.

The selected dose may be administered to a warm-blooded animal or mammal, for example, a human patient, in need of treatment mediated by inhibition of the binding of uPA to uPAR by any known method of administration, including topically or transdermally, e.g., as an ointment, cream or gel; orally; rectally, e.g., as a suppository; parenterally, by injection or continuously by infusion; intra-vaginally; intranasally; intrabronchially; intra-aurally; or intraocularly.

The cyclic peptide compounds of the invention may be further characterized as producing any one or more of inhibitor effect on uPA binding to uPAR, a proteolysis inhibitor effect, an inhibitory effect on programmed gene expression; an inhibitory effect on cell motility, migration and morphogenesis; an effect of slowing the activation of pro-growth factors to the active form of the growth factor; an anti-angiogenesis effect; an inhibitory effect on tumor metastasis; a lessening of retinal neovascularization; and a protective effect against inflammatory diseases such as arthritis. The compounds are especially useful in producing an anti-tumor effect in a vertebrate host harboring a tumor.

Further details of the production and purification of the compounds of the invention are given in the following illustrative specific example, which is not in any way intended to limit the scope of the invention.

EXAMPLE 1

Synthesis of:

Val-Ser-Asn-Lys-Tyr-Phe-Ser-Asn-Ile-His-Trp

The starting material was BOC-L-Cys(S-p-Methoxybenzyl)-O-resin, substituted at a level of 0.84 milliequivalent per gram of resin. Each of the remaining L-amino acids was added in sequence in a synthesis cycle consisting of:

1. TFA De-protection

The BOC protecting group was removed from the $\alpha$-amino nitrogen of the starting material by treating the resin with 50% trifluoroacetic acid (TFA) in dichloromethane (DCM) (two to three volumes per resin volume). The mixture was stirred at room temperature for 30 minutes and then drained. The resin was then washed once with an equal volume of isopropanol for one minute and washed twice with an equal volume of methanol, each wash taking one minute.

2. Coupling

The de-protected resin was washed twice with an equal volume of 10% triethylamine in DCM, each wash taking one minute, and washed twice with an equal volume of methanol, each wash taking one minute, and washed twice with an equal volume of DCM, each wash taking one minute. A BOC-protected amino acid (three equivalents, dissolved in DCM or in a mixture of DCM and N,N'-dimethylformamide (DMF)) and 1-hydroxybenzotriazole (1M solution in DMF, three equivalents) was added to the resin, and the mixture was stirred for a few seconds. Dicyclohexylcarbodiimide ("DCC") (1M solution in DCM, three equivalents) was then added, and the whole mixture was stirred for 60–120 minutes. The resin was washed twice with an equal volume of methanol and then washed twice with an equal volume of DCM. A small sample was taken for a ninhydrin test to assess the completeness of coupling. Generally, if incomplete, the coupling step 2 is repeated. If complete, the synthesis is continued with the capping step 3.

In the case of each of the five N-terminal amino acids, Val-Ser-Asn-Lys-Tyr, coupling was only partially complete and, therefore, was repeated at least once. The coupling of 4-bromobutyric acid was first attempted with DCC, as described above for the coupling step 2, but was incomplete. Three manual repeat couplings were performed using the symmetric anhydride method, the pentafluorophenylester method and, finally, with bromobutytyl chloride. A ninhydrin test following these procedures indicated virtually complete coupling.

All amino acids were used as $\alpha$-BOC derivatives. Side chain protecting groups were as follows:

| | |
|---|---|
| Cysteine | p-Methoxybenzyl |
| Tryptophan | N-Formyl |
| Histidine | Benzyloxymethyl |
| Asparagine | Xanthyl |
| Serine | O-benzyl |
| Tyrosine | 2-Bromo-Z |
| Lysine | 2-Chloro-Z |

Before coupling with bromobutyric acid, the formyl group of the tryptophan residue was removed by treatment with 20% piperidine in DMF at room temperature for 30 minutes.

3. Capping

The resin was stirred with an equal volume of acetic anhydride (20% solution in DCM) for 5 minutes at room temperature. The resin was washed twice with an equal volume of methanol and then washed twice with an equal volume of DCM.

4. HF Cleavage

The resin bearing the desired amino acid sequence (1.0 gram) was placed in a Teflon reaction vessel, and anhydrous anisole (1 mL) was added. The vessel was cooled with liquid $N_2$, and anhydrous HF (10 mL) was distilled into it. The temperature was raised with ice water to 0° C. The mixture was stirred at this temperature for one hour, and then the HF was distilled off at 0° C. The residue was washed with anhydrous ether, and the peptide was extracted with a 1:1 mixture of $CH_3CN:H_2O$.

5. Cyclization

The above peptide solution was diluted with $H_2O$ to a final volume of approximately 1000 mL, and the pH was adjusted with NaHCO$_3$ to 8.0. The cyclization was monitored by analytical HPLC. After 2–3 days, no further shift was observed in the chromatogram, and the cyclization was judged complete.

6. Purification

The turbid cyclization reaction mixture was filtered through a 1 μM filter. The filtrate was adjusted to pH 4.0 and loaded onto a Waters C18 preparative column (2 inches diameter, 15–20 μm particle size, 300 Å pore size). The loaded column was eluted with a two-component eluent applied as a linear gradient, starting with 15% of solution A in solution B and finishing with 40% of solution A in solution B. Solution A was 0.1% TFA in H$_2$O, and solution B was 0.1% TFA in CH$_3$CN. Fractions exhibiting purity equal to or better than that desired were pooled and lyophilized to render the purified final product as the trifluoroacetate salt.

We claim:

1. A method for inhibiting the specific binding of uPA to uPAR, comprising contacting uPA, a source of uPAR and an effective amount of a cyclic peptide compound of the formula:

wherein all of $X^1$ through $X^{11}$ represent L-series amino acids; and $X^1$ is Val or Ala; $X^2$ is Ser or Ala; $X^3$ is Asn or Gln; $X^4$ is Lys or His;

$X^5$ is Tyr, Trp, Phe, substituted Phe, di-substituted Phe, homophenylalanine, β(3-pyridyl)alanine, β-(2-thienyl)alanine, β-(1-naphthyl)alanine, or β-(2-naphthyl)alanine;

$X^6$ is Tyr, Trp, Phe, substituted Phe, disubstituted Phe, homophenylalanine, β-(3-pyridyl)alanine, β(2-thienyl)alanine, β(1-naphthyl)alanine, or β-(2-naphthyl)alanine;

$X^7$ is Ser or Ala; $X^8$ is Asn or Ala; $X^9$ is Ile, Leu, or Val; $X^{10}$ is His or Ala;

$X^{11}$ is Tyr, Trp, Phe, substituted Phe, di-substituted Phe, homophenylalanine, β-(3-pyridyl)alanine, β(2-thienyl)alanine, β-(1-naphthyl)alanine, or β-(2-naphthyl)alanine; and L is a linking unit, such that when $X^1$ and $X^{11}$ are linked, the linear dimension between the $C^\alpha$ carbon of amino acid $X^1$ and the $C^\alpha$ carbon of amino acid $X^{11}$ is between about 4 and 12 Ångstrom units, with the proviso that L does not comprise two cysteines linked by a disulfide bond, wherein said cyclic peptide compound inhibits said binding of uPA to uPAR.

2. The method of claim 1 wherein the linear dimension between the $C^\alpha$ carbon of amino acid $X^1$ and the $C^\alpha$ carbon of amino acid $X^{11}$ is between about 5 and 10 Ångstrom units.

3. The method of claim 1 wherein the linear dimension between the $C^\alpha$ carbon of amino acid $X^1$ and the $C^\alpha$ carbon of amino acid $X^{11}$ is between about 6 and 8 Ångstrom units.

4. The method of claim 1 wherein L is selected from the group consisting of:

—CO—CH$_2$—CH$_2$—CH$_2$—S—CH$_2$—CH(COOH)—NH—;

—CO—CH$_2$—CH$_2$—CH$_2$—CH$_2$—S—CH$_2$—CH(COOH)—NH—;

—CO—CH(NH$_2$)—CH$_2$—S—CH$_2$—CH$_2$—CH$_2$—NH—;

—CO—CH$_2$—CH$_2$—S—CH$_2$—CH$_2$—CH$_2$—NH—;

—CO—CH$_2$—CH$_2$—CH$_2$—CH$_2$—CH$_2$—CH$_2$—NH—;

—CO—CH$_2$—CH$_2$—S—CH$_2$—CH$_2$—CH(COOH)—NH—;

—CO—CH$_2$—CH$_2$—CH$_2$—CH$_2$—CH$_2$—CH(COOH)—NH—;

—CO—CH$_2$—S—CH$_2$—CH(COOH)—NH—;

—CO—CH$_2$—S—CH$_2$—CH$_2$—CH(COOH)—NH—; and

—CO—CH$_2$-meta-phenylene-CH$_2$—NH—.

5. The method of claim 1 wherein said compound has an IC$_{50}$ value of less than about $10^{-5}$ molar in a competitive binding assay to urokinase plasminogen activator receptor in vitro.

6. The method of claim 5 wherein said compound has an $IC_{50}$ value of less than about $10^{-6}$ molar in said assay.

7. The method of claim 6 wherein said compound has an $IC_{50}$ value of less than about $10^{-7}$ molar in said assay.

8. The method of claim 1 wherein said source of uPAR comprises cells that express uPAR.

9. The method of claim 8 wherein said contacting is in vivo.

10. A method to inhibit cell motility or cell migration that is associated with uPA-uPAR interaction, comprising carrying out the method of claim 8 wherein said cells are motile or able to migrate, such that the contacting of said cyclic peptide with said uPAR-expressing cells inhibits said motility or migration.

11. The method of claim 10 wherein said contacting is in vivo.

12. The method of claim 11 wherein said inhibition of cell motility or migration inhibits a process of tumor growth or metastasis which process is associated with uPA binding to uPAR.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 44 amino acids
      (B) TYPE: amino acid
      (C) STRANDEDNESS: single
      (D) TOPOLOGY: linear    (xi) SEQUENCE DESCRIPTION: SEQ ID NO: 1:

Ser Asn Glu Leu His Gln Val Pro Ser Asn Cys Asp Cys Leu Asn Gly
1               5                  10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile
            35                  40

(2) INFORMATION FOR SEQ ID NO: 2:

(i) SEQUENCE CHARACTERISTICS:
      (A) LENGTH: 21 amino acids
      (B) TYPE: amino acid
      (C) STRANDEDNESS: single
      (D) TOPOLOGY: both    (ix) FEATURE:
      (A) NAME/KEY: Disulfide-bond
      (B) LOCATION: 2..20
      (D) OTHER INFORMATION: /note= "present in oxidized cyclic
         form"

(xi) SEQUENCE DESCRIPTION: SEQ ID NO: 2:

Asp Cys Leu Asn Gly Gly Thr Ala Val Ser Asn Lys Tyr Phe Ser Asn
1               5                  10                  15

Ile His Trp Cys Asn
            20

(2) INFORMATION FOR SEQ ID NO: 3:

(i) SEQUENCE CHARACTERISTICS:
      (A) LENGTH: 11 amino acids
      (B) TYPE: amino acid
      (C) STRANDEDNESS: single
      (D) TOPOLOGY: linear    (xi) SEQUENCE DESCRIPTION: SEQ ID NO: 3:

Val Ser Asn Lys Tyr Phe Ser Asn Ile His Trp
1               5                  10

(2) INFORMATION FOR SEQ ID NO: 4:

(i) SEQUENCE CHARACTERISTICS:
            (A) LENGTH: 18 amino acids
            (B) TYPE: amino acid
            (C) STRANDEDNESS: single
            (D) TOPOLOGY: linear (xi) SEQUENCE DESCRIPTION: SEQ ID NO: 4:

Gly Thr Cys Val Ser Asn Lys Tyr Phe Ser Asn Ile His Trp Cys Asn
 1               5                  10                  15

Cys Pro (2) INFORMATION FOR SEQ ID NO: 5:

(i) SEQUENCE CHARACTERISTICS:
            (A) LENGTH: 49 amino acids
            (B) TYPE: amino acid
            (C) STRANDEDNESS: single
            (D) TOPOLOGY: linear (ix) FEATURE:
            (A) NAME/KEY: Disulfide-bond
            (B) LOCATION: group(11..19, 13..31, 33..42)

(xi) SEQUENCE DESCRIPTION: SEQ ID NO: 5:

Ser Asn Glu Leu His Gln Val Pro Ser Asn Cys Asp Cys Leu Asn Gly
 1               5                  10                  15

Gly Thr Cys Val Ser Asn Lys Tyr Phe Ser Asn Ile His Trp Cys Asn
                20                  25                  30

Cys Pro Lys Lys Phe Gly Gly Gln His Cys Glu Ile Asp Lys Ser Lys
             35                  40                  45

Thr (2) INFORMATION FOR SEQ ID NO: 6:

(i) SEQUENCE CHARACTERISTICS:
            (A) LENGTH: 11 amino acids
            (B) TYPE: amino acid
            (C) STRANDEDNESS: single
            (D) TOPOLOGY: circular (ix) FEATURE:
            (A) NAME/KEY: Modified-site
            (B) LOCATION: 1
            (D) OTHER INFORMATION: /note= "Val, Pro or Ala"

(ix) FEATURE:
            (A) NAME/KEY: Modified-site
            (B) LOCATION: group(2, 7)
            (D) OTHER INFORMATION: /note= "Ser or Ala"

(ix) FEATURE:
            (A) NAME/KEY: Modified-site
            (B) LOCATION: 3
            (D) OTHER INFORMATION: /note= "Asn or Gln"

(ix) FEATURE:
            (A) NAME/KEY: Modified-site
            (B) LOCATION: 4
            (D) OTHER INFORMATION: /note= "Lys or His"

(ix) FEATURE:
            (A) NAME/KEY: Modified-site
            (B) LOCATION: group(5, 6, 11)
            (D) OTHER INFORMATION: /note= "Tyr, Trp, Phe, substitued
                Phe, di-substituted Phe, homophenylalanine,
                beta-(3-pyridyl)alanine, beta-(2-thienyl)alanine,
                beta-(1-naphthyl)alanine or beta-(2-naphthyl)alanine"

(ix) FEATURE:
            (A) NAME/KEY: Modified-site
            (B) LOCATION: 8

(D) OTHER INFORMATION: /note= "Asn or Ala"

(ix) FEATURE:
            (A) NAME/KEY: Modified-site
            (B) LOCATION: 9
            (D) OTHER INFORMATION: /note= "Ile, Leu or Val"

(ix) FEATURE:
            (A) NAME/KEY: Modified-site
            (B) LOCATION: 10
            (D) OTHER INFORMATION: /note= "His or Ala"

(ix) FEATURE:
            (A) NAME/KEY: Cross-links
            (B) LOCATION: join(1, 11)
            (D) OTHER INFORMATION: /label= L
                /note= "linear dimension of
                linkage is between 4 and 12 Angstrom units"

(xi) SEQUENCE DESCRIPTION: SEQ ID NO: 6:

Xaa Xaa Xaa Xaa Xaa Xaa Xaa Xaa Xaa Xaa Xaa
1               5                   10

(2) INFORMATION FOR SEQ ID NO: 7:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note= "Val, Pro or Ala"

(ix) FEATURE:
        (A) NAME/KEY: Modified-site
        (B) LOCATION: group(2, 7)
        (D) OTHER INFORMATION: /note= "Ser or Ala"

(ix) FEATURE:
        (A) NAME/KEY: Modified-site
        (B) LOCATION: 3
        (D) OTHER INFORMATION: /note= "Asn or Gln"

(ix) FEATURE:
        (A) NAME/KEY: Modified-site
        (B) LOCATION: 4
        (D) OTHER INFORMATION: /note= "Lys or His"

(ix) FEATURE:
        (A) NAME/KEY: Modified-site
        (B) LOCATION: group(5, 6, 11)
        (D) OTHER INFORMATION:/note= "Tyr, Trp, Phe, substituted
            Phe, di-substituted Phe, homophenylalanine,
            beta-(3-pyridyl)alanine, beta-(2-thienyl)alanine,
            beta-(1-naphthyl)alanine or beta-(2-naphthyl)alanine"

(ix) FEATURE:
        (A) NAME/KEY: Modified-site
        (B) LOCATION: 8
        (D) OTHER INFORMATION: /note= "Asn or Ala"

(ix) FEATURE:
        (A) NAME/KEY: Modified-site
        (B) LOCATION: 9
        (D) OTHER INFORMATION: /note= "Ile, Leu or Val"

(ix) FEATURE:
        (A) NAME/KEY: Modified-site
        (B) LOCATION: 10
        (D) OTHER INFORMATION: /note= "His or Ala"

(xi) SEQUENCE DESCRIPTION: SEQ ID NO: 7:

Xaa Xaa Xaa Xaa Xaa Xaa Xaa Xaa Xaa Xaa Xaa

```
                1          5             10

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: single
        (D) TOPOLOGY: circular (ix) FEATURE:
        (A) NAME/KEY: Cross-links
        (B) LOCATION: 1..10

(xi) SEQUENCE DESCRIPTION: SEQ ID NO: 8:

Val Ser Asn Lys Tyr Phe Ser Asn Ile His
1               5                   10

(2) INFORMATION FOR SEQ ID NO: 9:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 9:

Val Ser Asn Lys Tyr
1               5
```